(12) United States Patent
Christensen (10) Patent No.: US 7,794,506 B2
(45) Date of Patent: Sep. 14, 2010

(54) MULTI-AXIAL PROSTHETIC ANKLE

(75) Inventor: Roland J. Christensen, Gunnison, UT (US)

(73) Assignee: Freedom Innovations, LLC, Irvine, CA (US)

( * ) Notice: Subject to any disclaimer, the term of this patent is extended or adjusted under 35 U.S.C. 154(b) by 0 days.

(21) Appl. No.: 12/211,600

(22) Filed: Sep. 16, 2008

(65) Prior Publication Data

US 2009/0082878 A1    Mar. 26, 2009

Related U.S. Application Data (60) Provisional application No. 60/994,468, filed on Sep. 18, 2007, provisional application No. 60/994,585, filed on Sep. 19, 2007.

(51) Int. Cl.
*A61F 2/66*    (2006.01)

(52) U.S. Cl. .......................................... 623/55; 623/49

(58) Field of Classification Search ............. 623/47–56; A61F 2/66, 2/68
See application file for complete search history.

(56) References Cited

U.S. PATENT DOCUMENTS

| | | | |
|---|---|---|---|
| 42,799 A | 5/1864 | Shepard | |
| 92,031 A | 6/1869 | Foster | |
| 292,800 A | 2/1884 | Furrer | |
| 497,026 A | 5/1893 | Judson | |
| 1,001,641 A | 8/1911 | Harrison | |
| 1,112,819 A * | 10/1914 | McFarland | 623/49 |
| 1,191,633 A | 7/1916 | White | |
| 1,289,580 A | 12/1918 | Vincenti | |
| 1,354,427 A | 9/1920 | Welter | |
| 1,779,765 A | 10/1930 | Eichhorn | |
| 1,996,874 A | 4/1935 | Mascau | |
| 2,036,830 A | 4/1936 | Rowley | |

(Continued)

FOREIGN PATENT DOCUMENTS

BR    9304225 A    7/1995

(Continued)

OTHER PUBLICATIONS www.micacorp.com/products/genesis2/, MICA Manufacturing Corporation, Genesis II Prosthetic Foot, Nov. 24, 2004, 1 page.

(Continued)

*Primary Examiner*—William H. Matthews
*Assistant Examiner*—Marcia Hoffman
(74) *Attorney, Agent, or Firm*—Thorpe North & Western, LLP (57) ABSTRACT

A prosthetic foot includes a rod having a substantially spherical head and a shank extending from the head. A connector is pivotally coupled to the spherical head of the rod. The connector has a coupling configured to attach to the stump of an amputee. A wear plate is disposed on the shank of the rod adjacent the connector. The wear plate is sized and shaped to contact the connector as the connector pivots on the spherical head of the rod. A spring is removably disposed on the shank of the rod and spaced apart from the wear plate a predetermined distance. The spring is compressible by the rod when the rod is disposed in a prosthetic foot and an axial load is applied to the rod.

17 Claims, 5 Drawing Sheets

U.S. PATENT DOCUMENTS

| | | | |
|---|---|---|---|
| 2,101,265 A | 12/1937 | Mercier |
| 2,379,538 A | 7/1945 | Meierhofer |
| 2,443,356 A | 6/1948 | Mathis |
| 2,453,969 A | 11/1948 | Carter |
| 2,470,480 A | 5/1949 | Fogg |
| 2,570,735 A | 10/1951 | Weise |
| 2,617,115 A | 11/1952 | Ellery |
| 2,640,200 A | 6/1953 | Wisbrun |
| 2,843,853 A | 6/1958 | Mauch |
| 2,973,969 A | 3/1961 | Thall |
| 3,206,235 A | 9/1965 | Albinson et al. |
| 3,379,430 A | 4/1968 | Ransom |
| 3,548,420 A | 12/1970 | Spence |
| 3,551,914 A | 1/1971 | Woodall |
| 3,754,286 A | 8/1973 | Ryan |
| 3,858,379 A | 1/1975 | Graves et al. |
| 3,871,032 A | 3/1975 | Karas |
| 3,874,004 A | 4/1975 | May |
| 3,906,552 A | 9/1975 | Weber |
| 3,920,610 A | 11/1975 | Wagner |
| 3,956,775 A | 5/1976 | Moore |
| 3,982,280 A | 9/1976 | Asbelle et al. |
| 4,089,072 A | 5/1978 | Glabiszewski |
| 4,328,594 A | 5/1982 | Campbell et al. |
| 4,341,222 A | 7/1982 | Gardineer et al. |
| 4,442,554 A | 4/1984 | Copes |
| 4,499,613 A | 2/1985 | Yarrow |
| 4,506,395 A | 3/1985 | Haupt |
| 4,517,968 A | 5/1985 | Greene et al. |
| 4,547,913 A | 10/1985 | Phillips |
| 4,606,332 A | 8/1986 | Gibson |
| 4,636,220 A | 1/1987 | Ziegelmeyer |
| 4,645,509 A | 2/1987 | Poggi et al. |
| 4,676,800 A | 6/1987 | Chen |
| 4,676,801 A | 6/1987 | Lundeen |
| 4,688,559 A | 8/1987 | Vito et al. |
| 4,721,510 A | 1/1988 | Cooper et al. |
| 4,764,172 A * | 8/1988 | McCoy | 623/49 |
| 4,793,450 A | 12/1988 | Harrison |
| 4,822,363 A | 4/1989 | Phillips |
| 4,852,863 A | 8/1989 | Savenije |
| 4,865,611 A | 9/1989 | Al-Turaiki |
| 4,865,612 A | 9/1989 | Arbogast et al. |
| 4,869,476 A | 9/1989 | Shtarkman |
| 4,938,775 A | 7/1990 | Morgan |
| 4,938,777 A | 7/1990 | Mason et al. |
| 4,959,073 A | 9/1990 | Merlette |
| 4,986,393 A | 1/1991 | Preukschat et al. |
| 5,019,109 A | 5/1991 | Voisin |
| 5,030,239 A | 7/1991 | Copes |
| 5,037,444 A | 8/1991 | Phillips |
| 5,062,859 A | 11/1991 | Naeder |
| 5,088,479 A | 2/1992 | DeToro |
| 5,112,356 A | 5/1992 | Harris et al. |
| 5,116,383 A | 5/1992 | Shorter et al. |
| 5,116,384 A | 5/1992 | Wilson et al. |
| 5,156,632 A | 10/1992 | Wellershaus |
| 5,181,932 A | 1/1993 | Phillips |
| 5,181,933 A | 1/1993 | Phillips |
| 5,217,500 A | 6/1993 | Phillips |
| 5,219,324 A | 6/1993 | Hall |
| 5,219,365 A | 6/1993 | Sabolich |
| 5,226,875 A | 7/1993 | Johnson |
| 5,258,039 A | 11/1993 | Goh et al. |
| 5,267,633 A | 12/1993 | Endo et al. |
| 5,290,319 A | 3/1994 | Phillips |
| 5,314,499 A | 5/1994 | Collier, Jr. |
| 5,376,133 A | 12/1994 | Gramnas |
| 5,376,139 A | 12/1994 | Pitkin |
| 5,376,141 A | 12/1994 | Phillips |
| 5,387,246 A | 2/1995 | Phillips |
| 5,405,408 A | 4/1995 | Pitkin |
| 5,405,411 A * | 4/1995 | McCoy | 623/49 |
| 5,425,781 A | 6/1995 | Allard et al. |
| 5,425,782 A | 6/1995 | Phillips |
| 5,429,588 A | 7/1995 | Young et al. |
| 5,443,528 A | 8/1995 | Allen |
| 5,443,529 A | 8/1995 | Phillips |
| 5,449,150 A | 9/1995 | Watanabe et al. |
| 5,458,656 A | 10/1995 | Phillips |
| 5,464,441 A | 11/1995 | Phillips |
| 5,482,513 A | 1/1996 | Wilson |
| 5,486,157 A | 1/1996 | DiBenedetto |
| 5,486,209 A | 1/1996 | Phillips |
| 5,507,838 A | 4/1996 | Chen |
| 5,509,936 A | 4/1996 | Rappoport et al. |
| 5,509,937 A | 4/1996 | Allard et al. |
| 5,509,938 A | 4/1996 | Phillips |
| 5,514,185 A | 5/1996 | Phillips |
| 5,514,186 A | 5/1996 | Phillips |
| 5,545,127 A | 8/1996 | DeToro |
| 5,549,714 A | 8/1996 | Phillips |
| 5,571,210 A | 11/1996 | Lindh |
| 5,571,213 A | 11/1996 | Allen |
| 5,593,455 A | 1/1997 | Phillips |
| 5,593,456 A | 1/1997 | Merlette |
| 5,593,457 A | 1/1997 | Phillips |
| 5,609,568 A | 3/1997 | Andrews |
| 5,645,138 A | 7/1997 | Tajima et al. |
| 5,653,767 A | 8/1997 | Allen et al. |
| 5,653,768 A | 8/1997 | Kania |
| 5,695,526 A | 12/1997 | Wilson |
| 5,725,598 A | 3/1998 | Phillips |
| 5,728,175 A | 3/1998 | Rincoe |
| 5,728,176 A | 3/1998 | Phillips |
| 5,728,177 A | 3/1998 | Phillips |
| 5,746,774 A | 5/1998 | Kramer et al. |
| 5,766,265 A | 6/1998 | Phillips |
| 5,766,704 A | 6/1998 | Allen et al. |
| 5,769,896 A | 6/1998 | Rosendahl et al. |
| 5,776,205 A | 7/1998 | Phillips |
| 5,779,735 A | 7/1998 | Molino |
| 5,800,564 A | 9/1998 | Gelineau |
| 5,800,565 A | 9/1998 | Biedermann |
| 5,800,569 A | 9/1998 | Phillips |
| 5,824,112 A | 10/1998 | Phillips |
| 5,888,238 A | 3/1999 | Phillips et al. |
| 5,893,891 A | 4/1999 | Zahedi |
| 5,897,515 A | 4/1999 | Willner et al. |
| 5,899,944 A | 5/1999 | Phillips |
| 5,913,902 A | 6/1999 | Geible |
| 5,944,679 A | 8/1999 | DeToro |
| 5,944,760 A | 8/1999 | Christensen |
| 5,957,981 A | 9/1999 | Gramnas |
| 5,976,191 A | 11/1999 | Phillips |
| 5,993,488 A | 11/1999 | Phillips |
| 6,007,582 A | 12/1999 | May |
| 6,019,741 A | 2/2000 | Prieskorn |
| 6,019,795 A | 2/2000 | Phillips |
| 6,071,313 A | 6/2000 | Phillips |
| 6,077,301 A | 6/2000 | Pusch |
| 6,083,184 A | 7/2000 | Kenosh |
| 6,099,572 A | 8/2000 | Mosler et al. |
| 6,120,547 A | 9/2000 | Christensen |
| 6,146,344 A | 11/2000 | Bader |
| 6,165,227 A | 12/2000 | Phillips |
| 6,187,052 B1 | 2/2001 | Molino et al. |
| 6,197,068 B1 | 3/2001 | Christensen |
| 6,206,934 B1 | 3/2001 | Phillips |
| 6,228,124 B1 | 5/2001 | Slemker et al. |
| 6,241,776 B1 | 6/2001 | Christensen |
| 6,245,035 B1 | 6/2001 | Schrijver |
| 6,254,643 B1 | 7/2001 | Phillips |
| 6,261,324 B1 | 7/2001 | Merlette |

| | | |
|---|---|---|
| 6,267,742 B1 | 7/2001 | Krivosha et al. |
| 6,280,479 B1 | 8/2001 | Phillips |
| 6,290,730 B1 | 9/2001 | Pitkin et al. |
| 6,302,858 B1 | 10/2001 | DeToro et al. |
| 6,306,178 B1 | 10/2001 | Kania et al. |
| D457,639 S | 5/2002 | McCoy |
| 6,402,790 B1 | 6/2002 | Celebi |
| 6,406,500 B1 | 6/2002 | Phillips |
| 6,443,993 B1 | 9/2002 | Koniuk |
| 6,443,995 B1 | 9/2002 | Townsend et al. |
| 6,514,293 B1 | 2/2003 | Jang et al. |
| 6,562,075 B2 | 5/2003 | Townsend et al. |
| 6,596,029 B1 | 7/2003 | Gramnas |
| 6,602,295 B1 | 8/2003 | Doddroe et al. |
| 6,663,673 B2 | 12/2003 | Christensen |
| 6,669,737 B2 | 12/2003 | Mosler et al. |
| 6,676,618 B2 | 1/2004 | Andersen |
| 6,676,708 B1 | 1/2004 | Laghi |
| 6,740,125 B2 | 5/2004 | Mosler |
| 6,793,683 B1 | 9/2004 | Laghi |
| 6,805,717 B2 | 10/2004 | Christensen |
| 6,869,451 B1 | 3/2005 | Laghi |
| 6,875,241 B2 | 4/2005 | Christensen |
| 6,875,242 B2 | 4/2005 | Christensen |
| 6,887,279 B2 | 5/2005 | Phillips et al. |
| 6,911,052 B2 | 6/2005 | Christensen |
| 6,929,665 B2 | 8/2005 | Christensen |
| 6,966,933 B2 | 11/2005 | Christensen |
| 7,172,630 B2 | 2/2007 | Christensen |
| 7,266,910 B2 | 9/2007 | Ingimundarson |
| 7,341,603 B2 | 3/2008 | Christensen |
| 7,419,509 B2 | 9/2008 | Christensen |
| 7,462,201 B2 | 12/2008 | Christensen |
| 2002/0077706 A1 | 6/2002 | Phillips |
| 2002/0133237 A1 | 9/2002 | Christensen |
| 2003/0019540 A1 | 1/2003 | Townsend et al. |
| 2003/0045944 A1 | 3/2003 | Mosler et al. |
| 2003/0120353 A1 | 6/2003 | Christensen |
| 2004/0064046 A1 | 4/2004 | Shehada |
| 2004/0068326 A1 | 4/2004 | Christensen |
| 2004/0102727 A1 | 5/2004 | Smits |
| 2004/0134500 A1 | 7/2004 | Ingimundarson et al. |
| 2004/0162623 A1 | 8/2004 | Phillips |
| 2005/0171618 A1 | 8/2005 | Christensen |
| 2005/0197717 A1 | 9/2005 | Ragnarsdottir et al. |
| 2005/0203640 A1 | 9/2005 | Christensen |
| 2005/0234378 A1 | 10/2005 | Ingimundarson et al. |
| 2006/0241783 A1 | 10/2006 | Christensen |

FOREIGN PATENT DOCUMENTS

| | | |
|---|---|---|
| BR | 9304552-2 | 11/1995 |
| CA | 2 266 113 | 10/1999 |
| DE | 295807 | 12/1916 |
| EP | 1 149 568 | 10/2001 |
| EP | 1340478 | 9/2003 |
| GB | 1191633 | 5/1970 |
| GB | 1550-658 | 8/1979 |
| GB | 2244006 | 11/1991 |
| IT | 556381 | 11/1958 |
| JP | 55112440 | 8/1980 |
| JP | 57040138 | 3/1982 |
| JP | 63231031 | 9/1988 |
| RU | 2033772 | 4/1995 |
| SU | 560606 | 7/1977 |
| WO | WO 94/10942 | 5/1994 |
| WO | WO9410942 | * 11/1994 |
| WO | WO 02/30340 | 4/2002 |
| WO | WO 03/003953 | 1/2003 |

OTHER PUBLICATIONS www.oandp.org/jpo/library/2000_01_09.asp, "Comparison of the Seattle Lite Foot and Genesis II Prosthetic Foot during walking and running." American Academy of Orthotists and Prosthetists, 2000, pp. 9-14, vol. 12, No. 1.

* cited by examiner

MULTI-AXIAL PROSTHETIC ANKLE

PRIORITY CLAIM

Priority is claimed to U.S. Provisional Patent Application Ser. No. 60/994,468, filed Sep. 18, 2007, and U.S. Provisional Patent Application Ser. No. 60/994,585, filed Sep. 19, 2007, which are herein incorporated by reference in their entirety.

BACKGROUND OF THE INVENTION

1. Field of the Invention

The present invention relates generally to a prosthetic foot with multi-axial rotation.

2. Related Art

Many individuals have lost a limb for various reasons including war, accident, or disease. In most instances these individuals are not only able to live relatively normal lives, but physically active lives as well. Oftentimes, these individuals are aided in their everyday lives by a prosthetic limb. The objective of prosthesis is to provide an artificial limb that simulates the function and natural feel of the replaced limb.

With respect to prosthetic feet, the development of a functional and natural artificial foot has been limited by material and imagination. Many designs have attempted to copy the anatomy of the foot or simulate its actions by replacing the bones and muscle with various mechanical simulation by replacing the entire foot with an energy storage element such as a spring. As the user steps onto the foot, the user's weight compresses the spring. As the user moves forward, the user's weight comes off the foot and the energy stored in the spring is used to propel the user forward.

Almost all of the past designs have focused on the major aspect of the prosthetic foot movement of the ankle or foot as it relates to walking or running. Few designs consider the lateral, or side to side rotation of the foot when the foot is used on varied or uneven terrain. It will be appreciated that the forefoot and heel of a natural foot rotates with a medial to lateral roll-over to accommodate variations in terrain. Most artificial feet of previous designs usually incorporate a unitary foot that is incapable of such movement.

Some designs have attempted to mimic the lateral rotation of the forefoot of a natural foot by splitting the forefoot region of the artificial foot longitudinally from the toe toward the heel, thereby effectively creating one or more "toes" on the prosthetic foot. This design is problematic, however, because the split creates at least two forefoot regions that can bend independent from one another and can result in an unnatural, out of balance feel to the user.

SUMMARY OF THE INVENTION

It has been recognized that it would be advantageous to develop a prosthetic foot with a multi-axial rotatable ankle for providing smooth and steady multi-axial rotation laterally and longitudinally of the foot to allow the wearer to maneuver uneven terrain. Additionally, it has been recognized that it would be advantageous to develop a prosthetic foot with a multi-axial rotatable ankle for providing smooth and steady multi-axial rotation to assist with a natural medial to lateral roll-over of the prosthetic foot in response to uneven terrain.

In one aspect, the present invention provides for an ankle for a prosthetic foot including a rod having a substantially spherical head and a shank extending from the head. A connector can be pivotally coupled to the spherical head of the rod. The connector can have a coupling configured to attach to the stump of an amputee. A wear plate can be disposed on the shank of the rod adjacent the connector. The wear plate can be sized and shaped to contact the connector as the connector pivots on the spherical head of the rod. A spring can be removably disposed on the shank of the rod and spaced apart from the wear plate a predetermined distance. The spring can be compressed by the rod when the rod is disposed in a prosthetic foot and an axial load is applied to the rod.

In another aspect, a foot member can be clamped between the spring and the wear plate by a fastener coupled to the shank of the rod.

Additional features and advantages of the invention will be apparent from the detailed description which follows, taken in conjunction with the accompanying drawings, which together illustrate, by way of example, features of the invention.

DETAILED DESCRIPTION

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention relates generally to an ankle for a prosthetic foot with variable toe-to-heel and medial-to-lateral rotation to provide for multi-axial rotation. The ankle can have a bolt or a rod with a spherical head and a shank that can be disposed through an elongated foot member in a prosthetic foot. A connector can be pivotally disposed on the spherical head of the rod. The connector can have a domed upper surface and an inverted pyramid coupling. The coupling can be attached to the stump of an amputee. The connector can pivot on the spherical head of the rod in a medial-to-lateral direction and in a toe-to heel direction. A wear plate can be disposed adjacent the connector and between the connector and the foot member of the prosthetic foot. The connector can contact the wear plate when the connector pivots about the spherical head. The wear plate can be sized and shaped to reduce contact of the connector with the foot member of the prosthetic foot so as to protect the foot member from wear and tear due to abrasion from the moving connector. A spring can be disposed on the shank of the rod on an opposite side of the foot member from the wear plate. A fastener, such as a nut, lock nut, pin, clip, or other type of fastener, can be disposed on the shank adjacent the spring. The fastener can apply a load on the spring member and clamp the foot member of the prosthetic foot between the spring and the wear plate. In this way, the spring member can apply an axial pre-load on the rod such that when a user walks on the prosthetic foot, opposing axial loads can be transferred to the rod and can compress the spring. Advantageously, when the spring is compressed, space is created between the connector and the wear plate which allows for multi-axial movement of the prosthetic foot with respect to the pyramid coupling and the stump of the amputee.

As illustrated in FIGS. 1-6, a prosthetic foot, indicated generally at 10, is shown in accordance with an embodiment of the present invention. The prosthetic foot 10 can include an elongated foot member 20, a connector, indicated generally at 40, for coupling the prosthetic foot to the stump of an amputee, and an ankle, indicated generally at 50.

The elongated foot member 20 can include an ankle section 22 to be coupled to the limb or stump of the amputee. In one aspect, the elongated foot member 20 can extend rearwardly from the ankle section 22 to a heel section 24, downwardly through the heel section, and forwardly through an arch section 24 to a toe section 26. The heel section 24 can be positioned at an approximate heel location of a natural foot. Likewise, the toe section 26 can be positioned at an approximate toe location of a natural foot. The toe location can be a region near the forward end of the foot where toes of a natural foot would be located.

The elongated foot member 20 can be substantially arcuate. The arc formed by the heel section 24 can be smoothly curved, or can be formed of both straight and curved sections. Thus, the elongated foot member 20 can form a curvilinear spring portion that can store and return energy to the user during walking, running, and other gait or bearing motions.

The elongated foot member 20 can be formed of a composite material. In one aspect, the foot member 20 can include a graphite fiber winding or mesh and a resin material that can be shaped and cured to form the elongated foot member 20. The foot member 20 may also be formed of other suitable materials as will be apparent to those skilled in the art.

It will be appreciated that while a single member prosthetic foot 10 is shown in FIGS. 1-4, multiple foot member prosthetic feet can also utilize the ankle 50 described herein. For example, the ankle 50 can be used with prosthetic feet that have upper and lower forefoot members. Additionally, a heel plate or sole plate can be disposed under the lower foot member, as known and practiced in the art.

The connector 40 can be coupled to the foot member 20 at the ankle section 22 and can attach to the stump of an amputee (not shown). The connector 40 can have an upper domed surface 42 and an inverted pyramid coupling 44 as is commonly used in attachment to the prepared stump of an amputee. The dome shaped upper surface 42 can facilitate articulation of the foot member 20 with respect to the stump of an amputee. The pyramid coupling 44 can fit into a corresponding socket in associated with the stump of the amputee. It will be appreciated that other types of couplings, as known in the art, can also be used with the connector of the present invention.

A wear plate 60 can be disposed between the connector 40 and the foot member 20. The wear plate 60 can be sized and shaped to protect the foot member 20 from wear due to movement between the connector 40 and the foot member 20. The wear plate 60 can be a metal material, such as steel. Other suitable materials with sufficient rigidity and resiliency, as known in the art, are also contemplated. In this way, as the connector 40 moves under the dynamic loads induced in the prosthetic foot during motion by the amputee, the connector 40 can rub against or abrade the wear plate 60 and not the composite material of the foot member 20. Thus, the wear plate 60 assists with wear resistance due to movement between the connector 40 and the foot 10 as the angle of the foot changes.

Figure 1:
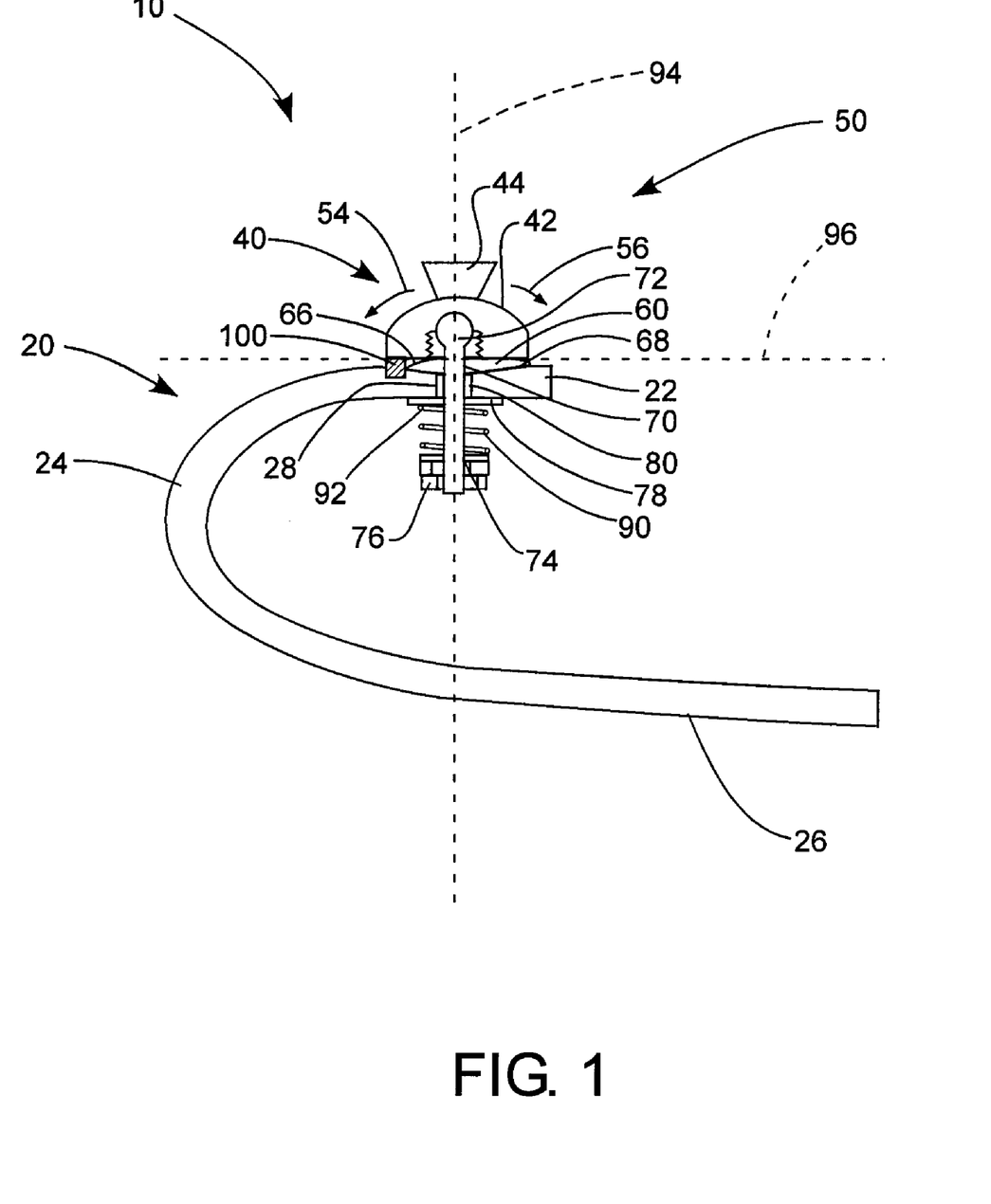
FIG. 1 is a cross section side view of a prosthetic foot with a multi-axial ankle in accordance with an embodiment of the present invention.
Figure 2:
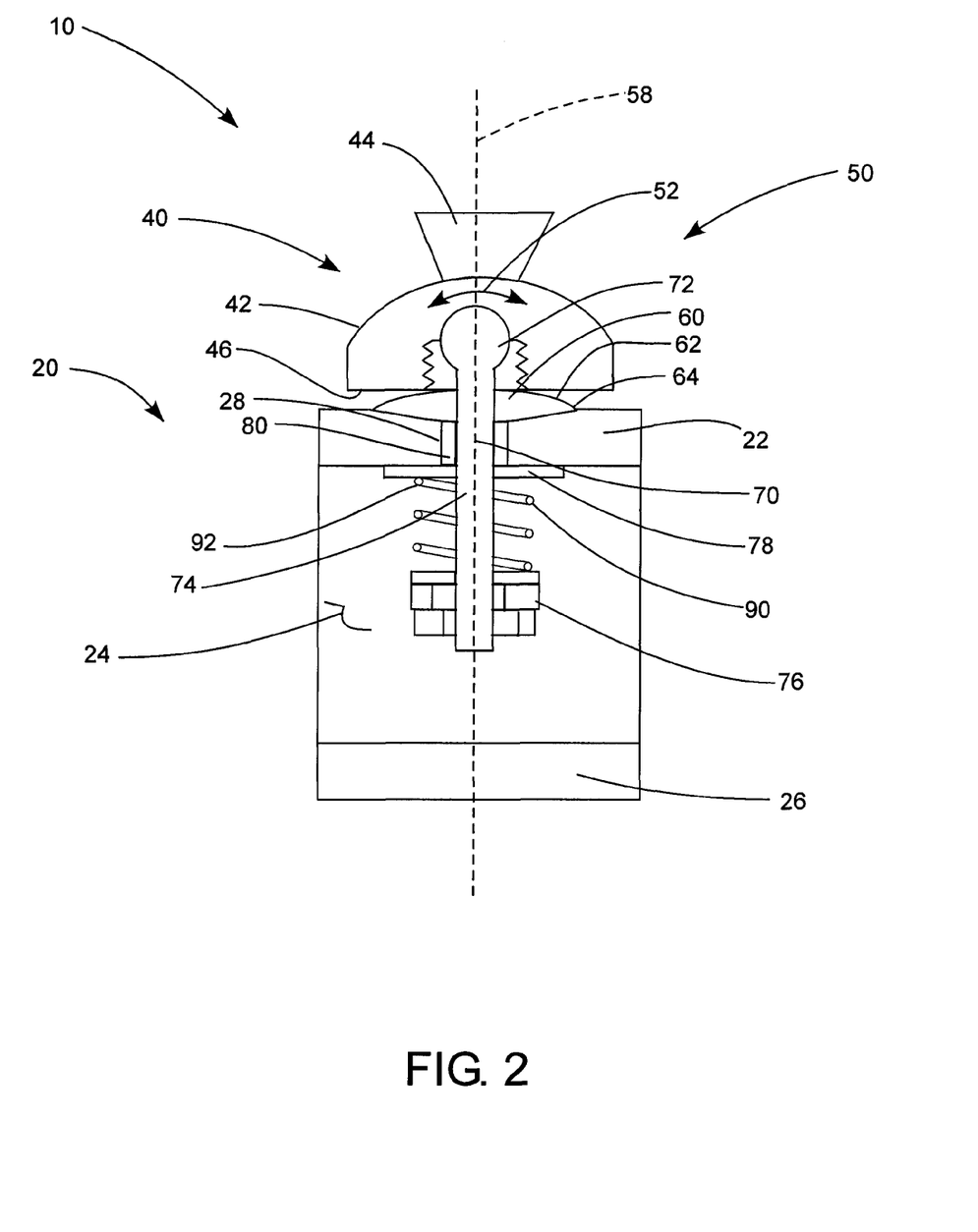
FIG. 2 is a cross section front view of the prosthetic foot of FIG. 1 taken along line 94.
Figure 3:
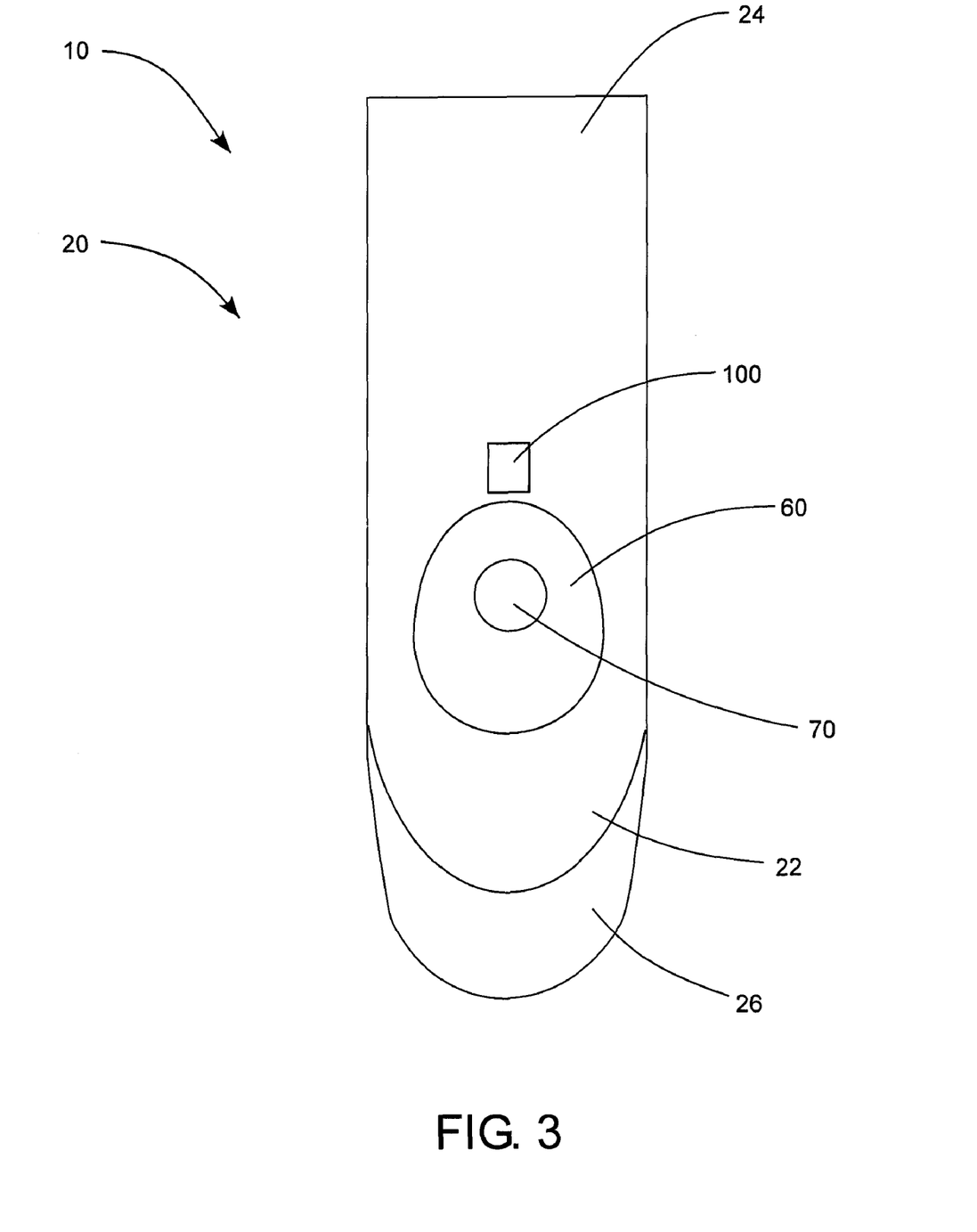
FIG. 3 is a cross section top view of the prosthetic foot of FIG. 1 taken along line 96.
Figure 4:
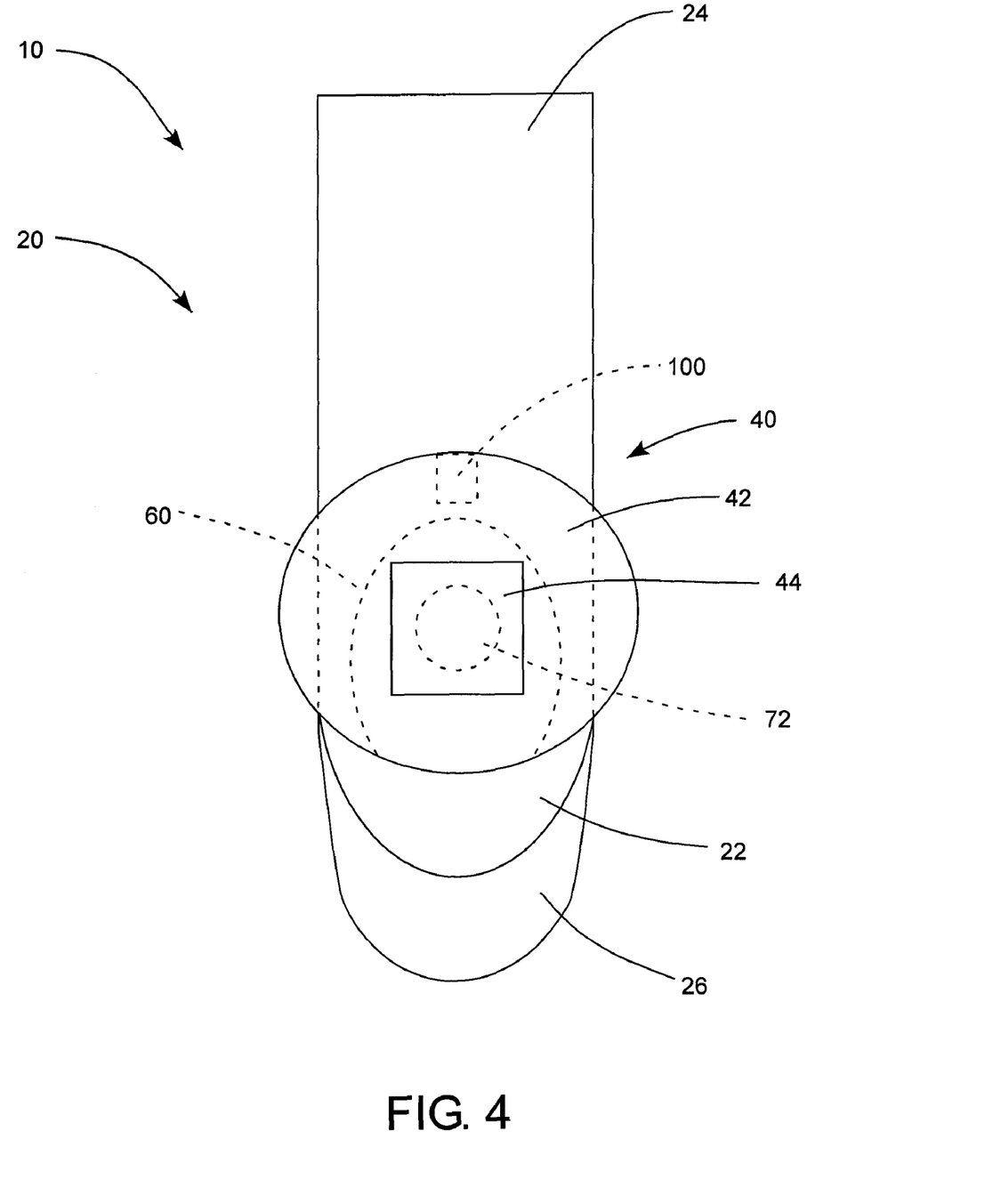
FIG. 4 is a top view of a prosthetic foot with a multi-axial ankle in accordance with an embodiment of the present invention.
Figures 5, 6:
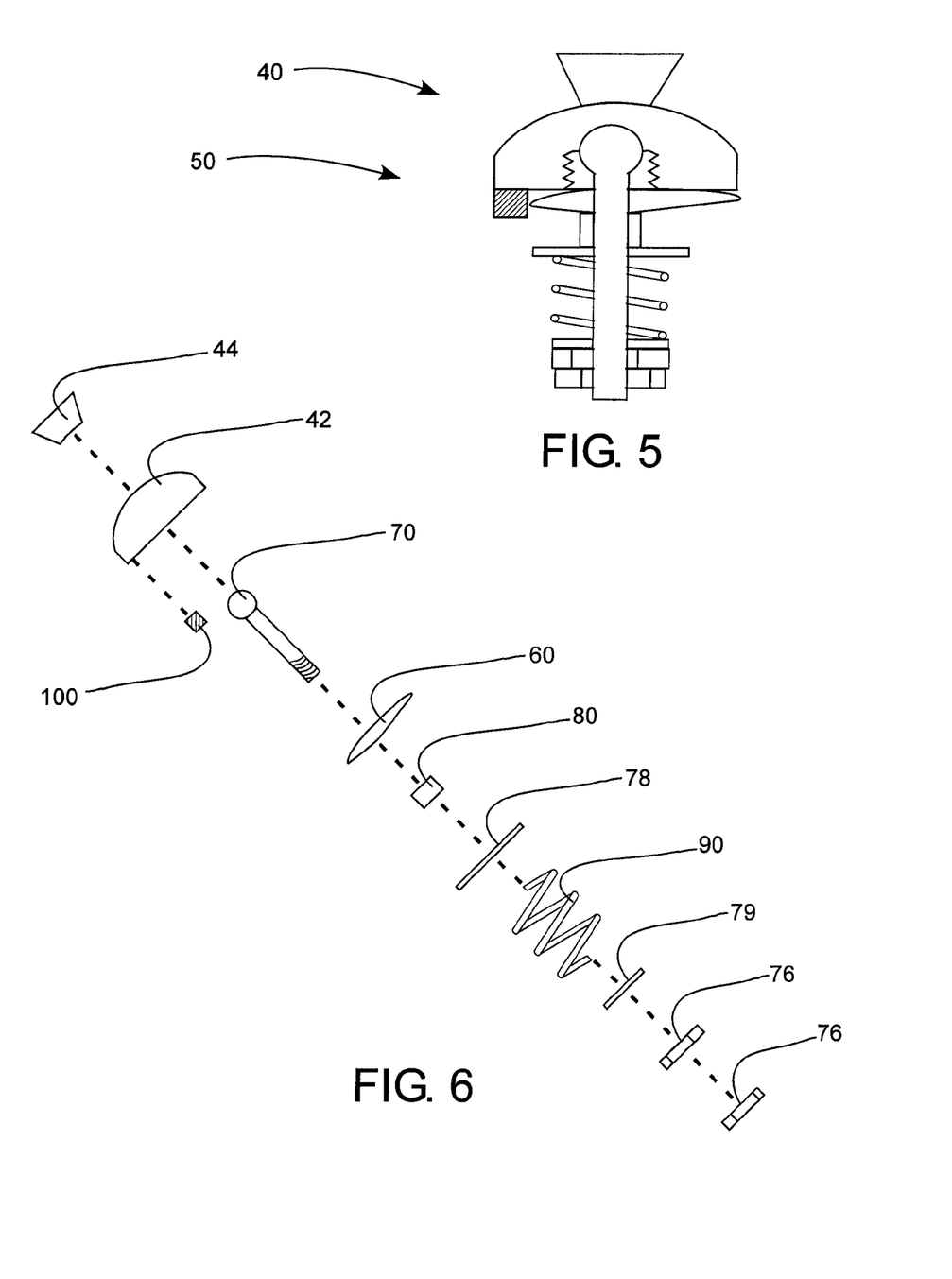
FIG. 5 is a cross section side view of a multi-axial ankle in accordance with an embodiment of the present invention.
FIG. 6 is an exploded view of the multi-axial ankle of FIG. 5.

The wear plate 60 can be shaped to facilitate rotation of the connector 40. For example, the wear plate 60 can have a substantially spherical or dome shaped upper surface 62. The wear plate upper surface 62 can contact a substantially flat lower surface 46 of the connector such that the substantially flat lower surface 46 of the connector 40 can pivot on the dome shaped upper surface 62 of the wear plate 60. Additionally, the width of the wear plate is smaller than a lateral width of the connector such that the longitudinal sides 64 of the wear plate are recessed under the connector so that the connector can rotate with relative ease in a medial to lateral direction with respect to the foot member, as indicated by arrow 52 in FIG. 2. Moreover, the back end 66 of the wear plate can be recessed under the connector so that the connector can rotate in a heel direction, indicated by the arrow at 54 in FIG. 1, with relatively greater resistance than in the medial to lateral direction. Furthermore, the front end 68 of the wear plate can be substantially flush with the edge 48 of the connector so that rotation of the connector in the toe direction, indicated by the arrow at 56 in FIG. 1, is restricted by relatively greater resistance than rotation in either the medial to lateral direction or the heel direction. In this way, the connector can rotate with relatively little stiffness or resistance in the medial to lateral direction, relatively more stiffness or resistance in the heel direction, and relatively more stiffness and greater resistance in the toe direction.

Additionally, the wear plate 60 can be shaped to vary a moment arm of the foot member 20 between toe-heel and medial-lateral loads. It will be appreciated that as weight is placed and shifted on the prosthetic foot 10 by the user, the moment arm between the application of the force on the foot member 20 and the pyramid coupling 44 of the connector 40 will change as the weight is shifted along the foot during the gait of the user. Thus, the wear plate 60 can, advantageously, be shaped to at least partially counter the length of the moment arm with respect to toe-heel and medial-lateral movement of the foot member with respect to the connector. In one aspect, the wear plate 60 can have a longer dimension which can be oriented towards the toe location to vary the moment arm of the foot member 20 between toe-heel and medial-lateral loads.

A bolt or rod 70 can extend through the foot member 20 at the ankle section 22. The rod 70 can have a spherical head 72 that can be disposed under the connector 40. The connector 40 can be pivotally coupled to the rod 70. In embodiments where the rod 70 includes a spherical head 72, the connector 40 can pivot on the spherical head 72. The rod 70 can also have a shank 74 that can extend from the spherical head 72 through an aperture 28 in the foot member 20 to an opposite side of the foot member from the spherical head. A fastener 76, such as nut, lock nut, double nut, pin, clip, or other type of fastener, can be disposed on the shank 74 at the opposite end from the spherical head. The shank 74 can include a threaded portion, hole, indentations, or other such features which facilitate fastening the fastener 76 to the shank 74. The fastener 76 can secure the rod 70 to the foot member 20. Additionally, it may be desirable to utilize a washer 79 on the rod 70, between the fastener 76 and the spring 90.

A bushing 80 can be disposed in the aperture 28 of the foot member 20 to protect the composite material of the foot member from abrasion from the shank 74 of the rod 70. The bushing 80 can be sized and shaped to receive the shank 74 of the rod through the bushing. In one aspect, the bushing 80 can be formed of a polymeric material, such as urethane.

A spring 90 can be coupled to the shank 74 of the rod 70. The spring 90 can be removable to facilitate repair, replacement, or other maintenance. The spring 90 can be positioned on the shank 74 on the opposite side of the foot member 20 from the spherical head 72. The fastener 76 can retain the spring 90 on the shank 74 and can compress the spring against the foot member 20. In this way, the spring 90 can be preloaded to counteract applied loads from the foot during use by the amputee. The spring 90 can be further compressed between the fastener 76 and the foot member 20 when an axial load is applied to the rod 70 during use of the prosthetic foot 10.

In one aspect, the spring 90 can be a Belleville or cupped spring washer. In another aspect, the spring 90 can be a helical die spring 92. The helical die spring 92 can be positioned between the fastener 76 and a washer 78. The washer 78 can rest against the foot member 20 and can protect the composite material of the foot member from abrasive movements by the helical die spring 92. It will be appreciated that any of a variety of suitable spring types, such as coil springs, compression springs, torsion springs, cupped spring washers, pneumatic spring cylinders, and the like can also be used.

A pin 100 can be coupled to the connector 40 and disposed adjacent the wear plate 60 behind the rod 70. The pin 100 can extend from the connector 40 into the foot member 20. The pin 100 can be sized and shaped to restrict or reduce rotation of the foot member 20 with respect to the connector 40 about a longitudinal axis, indicated by a dashed line at 58 in FIG. 2, of the pyramid connector 44. In this way, the ankle 50 of the present invention can provide medial-to-lateral rotation and heel rotation when the user is traversing uneven terrain with the prosthetic foot 10, or when the user puts an indirect lateral or medial load on the foot as when side-stepping or turning mid-gait, while restricting spinning or rotation of the foot 10 about the longitudinal axis 58 of the pyramid coupling 44 or stump of the amputee.

In use, as the user places an applied load on the foot member 20 during a gaited movement, the load produces a moment in the foot member 20. The moment in the foot member, in turn, produces an axial tension force in the spherical head 72 of the rod 70. The axial tension force in the rod 70 compresses the spring 90 such that the rod is pushed upward creating a space between the connector 40 and the wear plate 60. The space between the connector 40 and the wear plate 60 allows for multi-axial rotation or pivoting movement of the foot member 20 with respect to the pyramid coupling 44 disposed on the connector 40. Thus, as the foot 10 is dynamically loaded during the gait of the user, the foot can pivot or rotate in a toe-to-heel or medial-to-lateral direction according to the terrain or gait angle of the user.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

What is claimed is:

1. A prosthetic foot, comprising:
   a) an elongated foot member, extending between a toe section positioned at a toe location of a natural foot and an ankle section positioned at an ankle location of a natural foot;
   b) a connector coupled to the foot member at the ankle section and configured to attach to the stump of an amputee;
   c) a rod having a shank extending from the connector through the foot member at the ankle section to an opposite side of the foot member opposite the connector;
   d) a spring disposed on the shank of the rod on the opposite side of the foot member opposite the connector, the spring being compressible by the rod when an axial load is applied to the rod; and
   e) a wear plate disposed between the connector and the foot member, the connector having a lower surface that contacts and rubs against the upper surface of the wear plate, wherein the wear plate has a smaller lateral width than the lower surface of the connector with a front edge being substantially flush with a front edge of the connector.

2. A prosthetic foot in accordance with claim 1, wherein the spring is a helical die spring.

3. A prosthetic foot in accordance with claim 1, wherein the rod has a spherical head disposed in the connector, and wherein the connector is configured to pivot on the spherical head.

4. A prosthetic foot in accordance with claim 1, further comprising a pin extending from the connector to the foot member to resist rotation of the foot member with respect to the connector about the rod.

5. A prosthetic foot in accordance with claim 1, wherein the wear plate is sized and shaped to vary a rotational stiffness of the connector with respect to the foot plate, having greater stiffness or resistance in a heel direction than in a medial to lateral direction, and a greater stiffness or resistance in a toe direction than in the medial to lateral direction.

6. A prosthetic foot in accordance with claim 1, wherein the wear plate has a longer dimension oriented towards the toe location longer than a dimension oriented in a medial to lateral direction to vary a moment arm of the foot member between toe-heel and medial-lateral loads.

7. A prosthetic foot in accordance with claim 1, wherein the connector is configured to pivot upon the spherical head and wherein the wear plate is sized and shaped to contact the connector as it pivots.

8. A prosthetic foot in accordance with claim 1, further comprising a bushing disposed in an aperture of the foot member sized and shaped to receive the shank of the rod therethrough.

9. A prosthetic foot in accordance with claim 1, wherein the spring is removable.

10. A prosthetic foot, comprising:
   a) an elongated foot member, extending between a toe section positioned at a toe location of a natural foot and an ankle section positioned at an ankle location of a natural foot;
   b) a connector coupled to the foot member at the ankle section and configured to attach to the stump of an amputee;
   c) a wear plate disposed between the connector and the foot member, sized and shaped to protect the foot member from wear due to movement between the connector and the foot member;

d) a spherical head rod, extending from the connector through the foot member at the ankle section, the spherical head rod having a spherical head disposed in the connector and a shank extending from the spherical head to an opposite side of the foot member opposite the connector; and e) a spring disposed on the shank of the rod on the opposite side of the foot member opposite the connector and between the foot member and an end of the rod opposite the spherical head, the spring being compressible by the rod against the foot member when an axial load is applied to the rod, wherein the wear plate is sized and shaped to vary a rotational stiffness of the connector with respect to the foot plate, having a greater stiffness or resistance in a heel direction than in a medial to lateral direction, and a greater stiffness or resistance in a toe direction than in the medial to lateral direction.

11. A prosthetic foot in accordance with claim 10, wherein the spring is a helical die spring.

12. A prosthetic foot in accordance with claim 10, wherein the wear plate is disposed on the shank of the rod adjacent the connector, and sized and shaped to contact the connector as the connector pivots on the rod.

13. A prosthetic foot in accordance with claim 12, further comprising a pin extending between the connector and the foot member.

14. A prosthetic foot in accordance with claim 12, wherein the wear plate has a longer dimension oriented towards a toe location of the foot member longer than a dimension oriented in a medial to lateral direction to vary a moment arm of the prosthetic foot member between toe-heel and medial-lateral loads.

15. A prosthetic foot in accordance with claim 12, further comprising a bushing disposed about the shank between a lower surface of the connector and the spring member, the bushing being disposable in the prosthetic foot member.

16. A prosthetic foot in accordance with claim 10, wherein the spring is removable.

17. A prosthetic foot, comprising:

a) an elongated foot member, extending between a toe section positioned at a toe location of a natural foot and an ankle section positioned at an ankle location of a natural foot;

b) a connector coupled to the foot member at the ankle section and configured to attach to the stump of an amputee;

c) a wear plate disposed between the connector and the foot member, sized and shaped to protect the foot member from wear due to movement between the connector and the foot member;

d) a rod, extending from the connector through the foot member at the ankle section, the rod having a spherical head pivotally disposed in the connector and a shank extending from the spherical head to an opposite side of the foot member opposite the connector;

e) a spring disposed on the shank of the rod on the opposite side of the foot member opposite the connector and disposed between the foot member and an end of the rod opposite the spherical head, the spring being compressible by the rod against the foot member when an axial load is applied to the rod, wherein the wear plate has a smaller lateral width than a lower surface of the connector and a front edge being substantially flush with a front edge of the connector; and 1) a pin extending between the connector and the foot member to restrict toe-heel rotation of the prosthetic foot.

* * * * *